United States Patent [19]

Callicrate

[11] Patent Number: 5,403,325
[45] Date of Patent: Apr. 4, 1995

[54] POWER CASTRATION TOOL AND METHOD

[76] Inventor: Michael P. Callicrate, P.O. Box 602, St. Francis, Kans. 67756

[21] Appl. No.: 86,806

[22] Filed: Jul. 2, 1993

Related U.S. Application Data

[63] Continuation-in-part of Ser. No. 807,727, Dec. 16, 1991, Pat. No. 5,236,434.

[51] Int. Cl.6 .............................................. A61B 17/00
[52] U.S. Cl. .................................. 606/135; 606/139; 606/141; 606/151
[58] Field of Search .................... 606/1, 103, 110, 113, 606/135, 139, 140, 141, 151; 81/467, 469, 480

[56] References Cited

U.S. PATENT DOCUMENTS

| 612,569 | 10/1898 | Moscrop . | |
|---|---|---|---|
| 1,885,945 | 11/1932 | Ransy . | |
| 2,487,425 | 11/1949 | Collins . | |
| 3,547,124 | 12/1970 | Fergusson . | |
| 3,687,138 | 8/1972 | Jarvik . | |
| 3,726,278 | 4/1973 | Scott . | |
| 3,813,983 | 6/1974 | Paul | 81/469 |
| 4,220,155 | 9/1980 | Kimberling et al. . | |
| 4,572,179 | 2/1986 | Tietelbaum et al. . | |
| 4,682,716 | 7/1987 | Morellini . | |
| 4,691,704 | 9/1987 | Wadsworth . | |
| 4,721,169 | 1/1988 | Nagasawa et al. | 81/469 |
| 4,966,057 | 10/1990 | Koppatsch | 81/469 |
| 4,966,600 | 10/1990 | Songer et al. | 606/74 |
| 4,986,369 | 1/1991 | Fushiya et al. | 81/467 |
| 5,163,948 | 11/1992 | Kummer | 606/151 |
| 5,188,637 | 2/1993 | Wadsworth | 606/151 |

*Primary Examiner*—Stephen C. Pellegrino
*Assistant Examiner*—Jeffrey A. Schmidt
*Attorney, Agent, or Firm*—Sheridan Ross & McIntosh

[57] ABSTRACT

A method and apparatus (10) for applying a band (18) of ligature material to an animal body part is provided, such method employing a motor to facilitate the winding of ligature material. The apparatus (10) includes a winding assembly (14) for winding the band (18), wherein a loop (20) of the band (18) is tightened by winding the band (18). A crimping assembly (16) for crimping a grommet (32) to secure the loop (20) is also disclosed. The invention allows the loop (20) to be quickly and tightly secured using pneumatic/electric tools or motors.

32 Claims, 5 Drawing Sheets

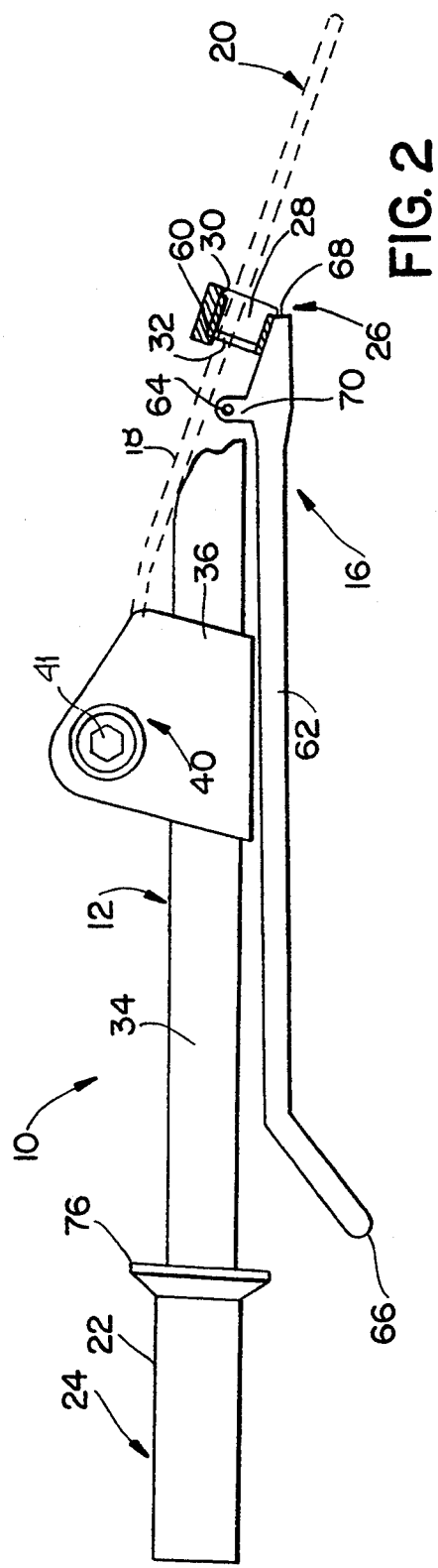
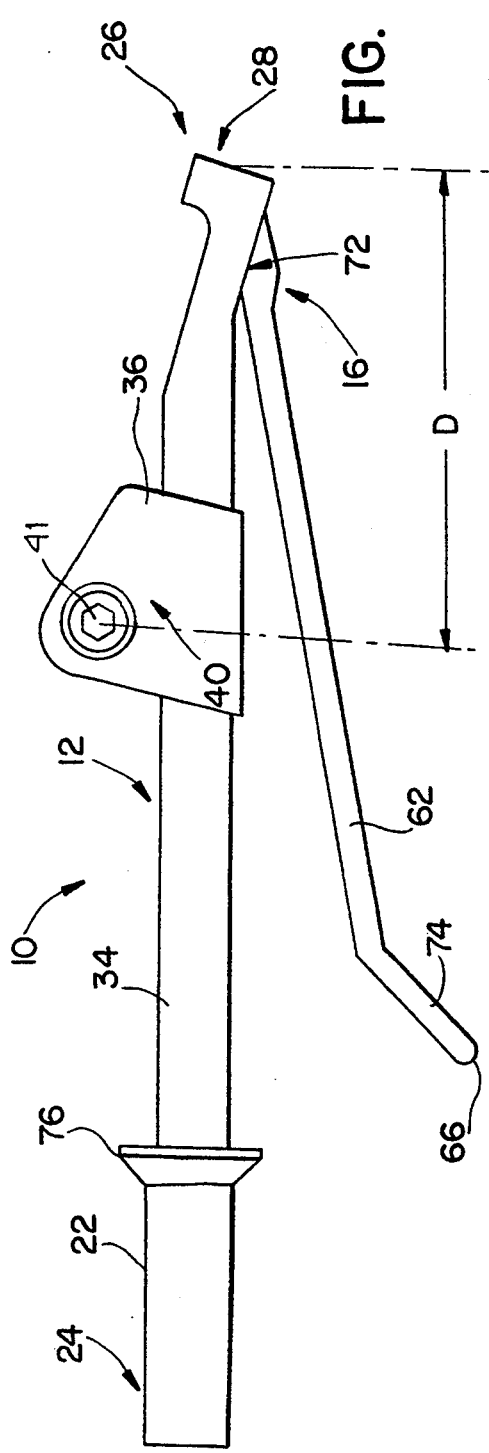

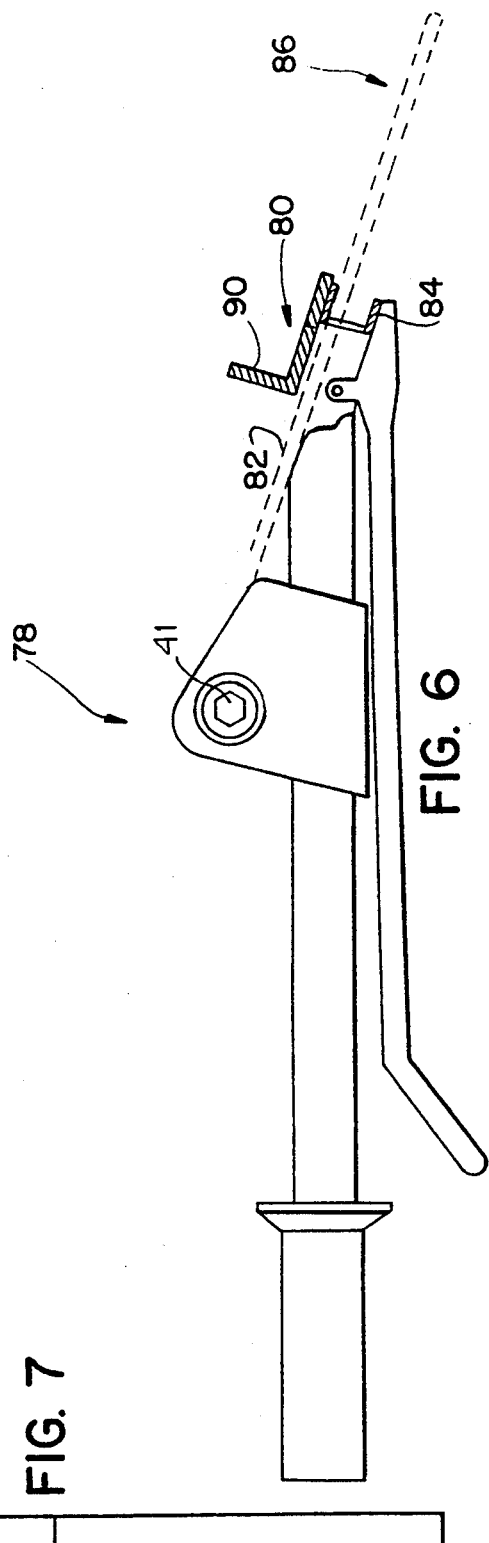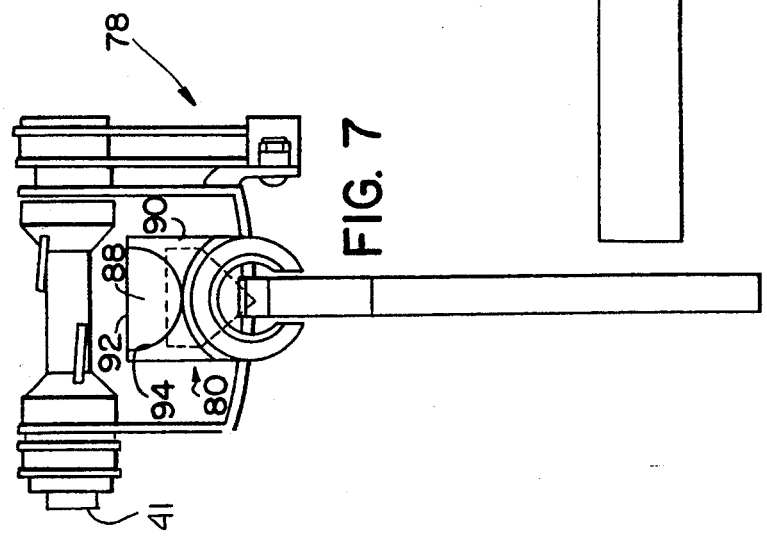

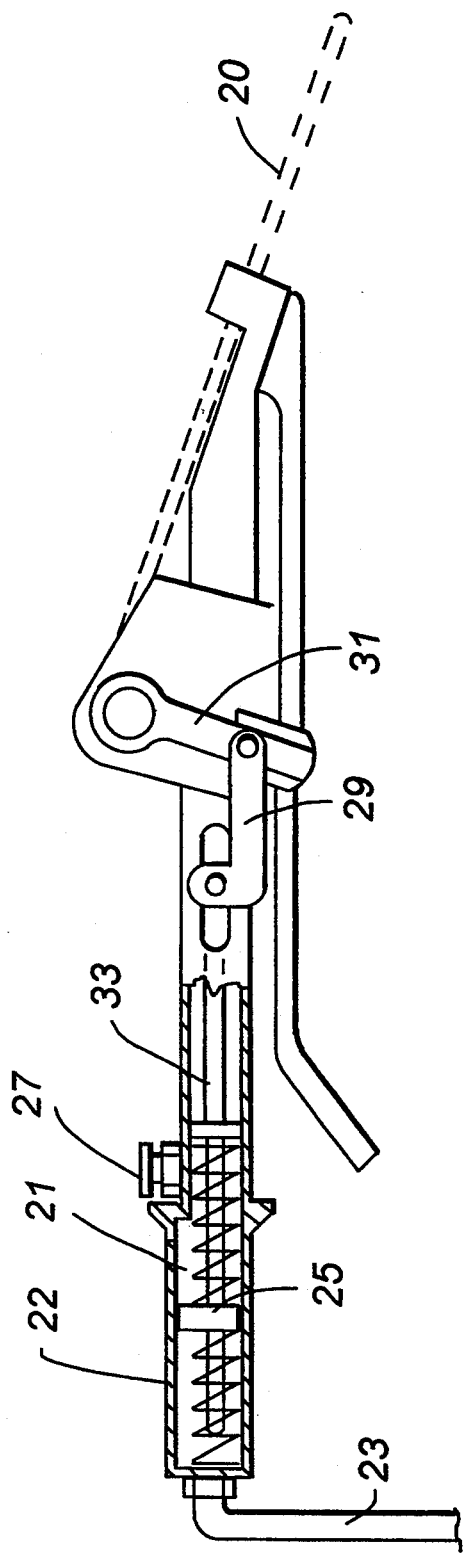
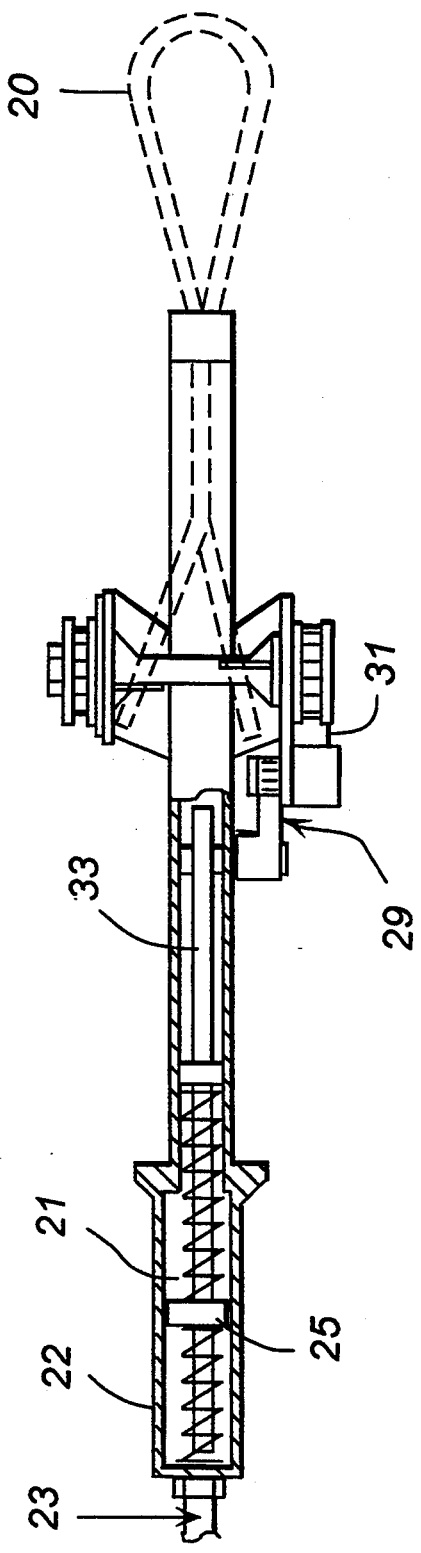
Fig. 8
Fig. 9

POWER CASTRATION TOOL AND METHOD

RELATED APPLICATION

The present application is a continuation-in-part of Ser. No. 807,727, now U.S. Pat. No. 5,236,434, filed Dec. 16, 1991, and entitled "METHOD AND APPARATUS FOR LIGATING A BODY PART" by Callicrate. U.S. Pat. No. 5,236,434 is incorporated herein by reference in its entirety.

FIELD OF THE INVENTION

This invention relates in general to ligature tools and in particular to a method and apparatus for applying a ligature band to an animal body part.

BACKGROUND OF THE INVENTION

A common method for the removal of a body part is ligation. Ligation is a process in which a band or cord is fastened to the body part to be removed in order to constrict it, thus cutting off the supply of blood and systemic support. The body part thereafter atrophies and drops away from the body. Ligation has been used for many purposes including castration and the removal of horns, tails or other body parts from animals.

Ligation has a number of advantages over surgical procedures for such applications. First, ligation has a safety advantage in that the animal normally does not become susceptible to infection. For example, in the case of castration of bulls, a period of about two weeks to a month typically passes between the time that the ligature is attached to the scrotum and the time that the scrotum drops off. During this time the area adjacent the ligature heals, thus reducing the likelihood of infection. Another advantage of ligation is that ligation can be performed quickly by non-expert personnel, thereby reducing costs. In addition, when the ligature is sufficiently tight, ligation can generally be performed with little stress on the animal because the body part numbs quickly after the blood supply is cut off.

According to one method of ligation, an endless loop of elastic band is used to cut off the blood supply to the body part to be removed. Because the band is endless, the band is positioned by passing the band loop over the body part. This method has the disadvantage that it is difficult to attach the ligature band such that it is sufficiently tight. For example, when an endless band is used to castrate bulls, the band must be stretched to pass over the scrotal sac and its contents and then released to engage the sac at the desired position. The tightness of the band when positioned is therefore limited by the band's elasticity. In addition, because an endless ligature band generally cannot be tightened, the size of the band loop can only be roughly matched to a particular application. That is, the band is usually selected from a limited number of discrete band sizes. Because of the difficulty in tightly applying endless bands, such bands may fail to sufficiently cut off the blood supply resulting in prolonged stress to the animal and an increased likelihood of swelling and/or infection. In addition, there is a greater chance that the animal will intentionally or unintentionally displace a loose band.

Another ligation method is disclosed in U.S. Pat. No. 4,691,704. A loop of a ligature elastomeric band is formed around the body part to be ligated, and then an end portion of the band is attached to a tightening rod. The tightening rod can then be retracted in a substantially linear fashion by successive pulls on a trigger mechanism, thereby tightening the loop. However, the process of tightening the loop through successive pulls on the trigger mechanism is time consuming and the animal must therefore be restrained for a longer period of time. In addition, the tension which can be imparted to the band, and the tightness of the loop, are limited by the hand strength of the user. Moreover, relatively large frictional and abrasive forces are exerted on the band where the band is attached to the tightening rod, thereby increasing the likelihood of damage to the elastomeric material causing breakage before the desired tension is achieved. Additionally, due to the design of the ligature tool, an operator is limited in the extent a band can be tightened. Once an operator has fully retracted the tightening rod, the loop's tightness cannot be increased.

The inability to achieve relatively quick and complete occlusion of both venous and arterial pressure within the body part being ligated may result in the venous pressure alone being shut off, thereby permitting the stronger arterial pressure to fill the bony part with blood. This, in turn, can lead to swelling of the body part and failure of the ligation process, causing consequential pain to the animal.

SUMMARY OF THE INVENTION

The present invention discloses a method and apparatus for ligation which avoids or alleviates the problems discussed above. The present invention allows a ligature band to be tightly attached to an animal body part thereby reducing the likelihood off swelling, infection and/or prolonged stress to the animal. The present invention also allows the band to be tightened quickly thereby reducing the length of time that the animal must be restrained.

According to the present invention, a method and apparatus for ligation is provided. The method includes the steps of forming a loop about the body part with a band of ligature material and winding the band to tighten the loop. Preferably, the band is tightened by securing the band to a spool and then rotating the spool to wind the band. After the loop is tightened, the loop can be secured by crimping a grommet so that the band is secured therein.

A tool constructed in accordance with an embodiment of the present invention includes a receiving device for receiving a band of ligature material, wherein the band forms a loop external to the receiving device. A winding assembly is interconnected to the receiving device such that the loop is tightened by winding the band.

Preferably, the winding assembly includes a spool that facilitates the securing of a band thereabout as the spool is rotated. A ratchet mechanism can be employed to provide for one way rotation of the spool. In a preferred embodiment, the tool is operated by pneumatic or electrical motors or by power tools which function to wind the band around the spool to achieve a desired loop tightness or tension. The tightness of the loop can be modified by adjusting either the pneumatic/electrical winding device so that winding of ligature material ceases at a predetermined tension, or by providing a clutch mechanism on the tool itself.

BRIEF DESCRIPTION OF THE DRAWINGS

FIG. 2 is a side view, partially cut away, of the apparatus of FIG. 1;

FIG. 3 is a side elevational view of the apparatus of FIG. 1 with the crimping arm in a deflected position;

FIG. 6 is a side view, partially cut away, of an apparatus constructed in accordance with the present invention showing a cutting assembly;

FIG. 7 is a front view of the apparatus of FIG. 6; and

FIG. 8 is a side partial section elevational view of one embodiment of the present invention in which a power winding source is integral with the ligation tool itself.

FIG. 9 is a top partial section view of one embodiment of the present invention in which a power winding source is integral with the ligation tool itself.

DETAILED DESCRIPTION OF THE INVENTION

Figure 1:
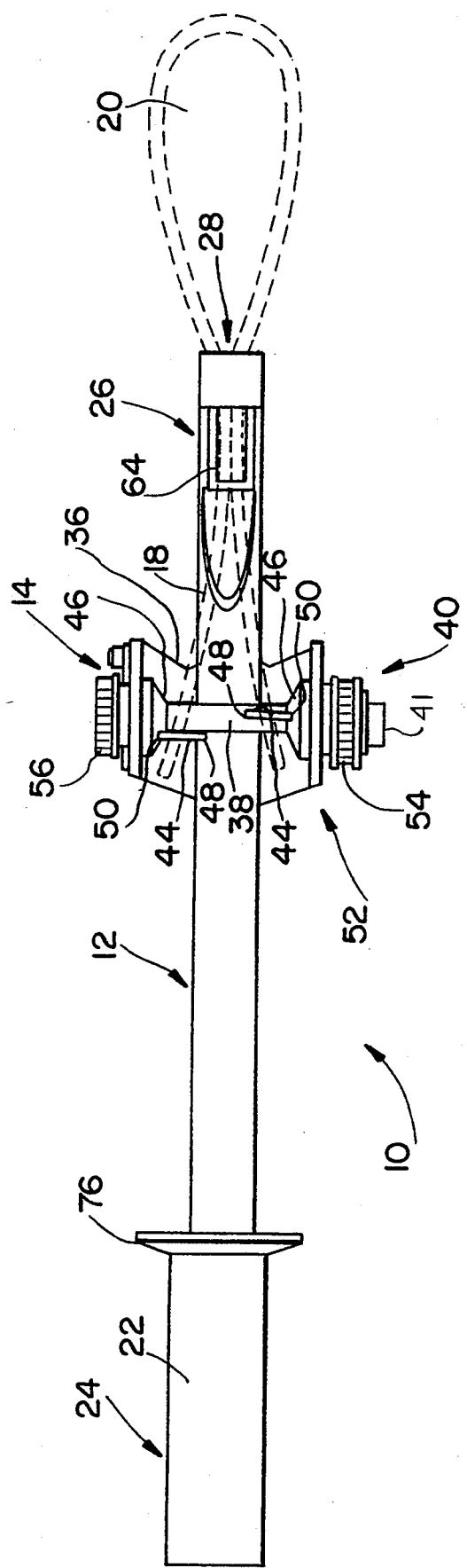
FIG. 1 is a top view of an apparatus constructed in accordance with the present invention.
Figure 4:
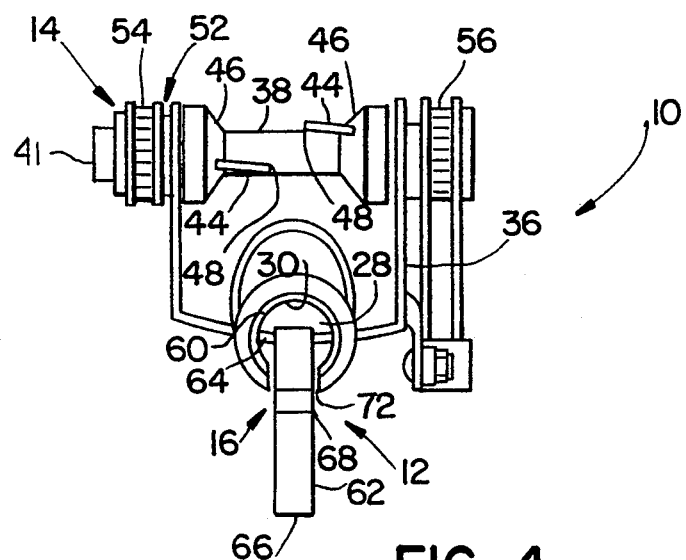
FIG. 4 is a front elevational view of the apparatus of FIG. 1.

Referring to FIGS. 1-4, an apparatus constructed in accordance with an embodiment of the present invention is generally identified by the reference numeral 10. As shown, the apparatus 10 comprises a tool body 12, a winding assembly 14 and a crimping assembly 16.

The body 12 receives a band 18 of ligature material, wherein a loop 20 of ligature material is formed external to the apparatus 10 about an animal body part to be removed. The loop 20 is then progressively tightened by winding the band 18 about winding assembly 14 to substantially cut off blood flow and systemic support to the animal body part. Preferably, the ligature material comprises an elastomeric material such as surgical tubing. However, because of the large tightening forces which can be achieved with the apparatus 10, relatively inelastic band materials such as rope and/or wire may be successfully employed.

The tool body 12, which may comprise steel or other material having sufficient strength to withstand the forces encountered during ligation procedures, has a handle 22 at a first end portion 24 thereof and a second end portion 26 which is adapted to receive the band 18 of ligature material. The handle 22 may be contoured for optimal handling by the user. In the illustrated embodiment, the second end portion 26 includes a passageway 28 sufficient to allow passage of the band 18 therethrough. The second end portion 26 can also include a receptacle 30 adapted to hold a grommet 32 which can be crimped, as will be described below, to secure the band 18 after the loop 20 has been tightened. It will be appreciated that the band 18 of ligature material is pulled rearwardly through the passageway 28 towards the winding assembly 14 as the loop 20 is tightened. As illustrated, the second end portion 26 may be angled relative to a longitudinal portion 34 of the body 12, the angle preferably selected such that a longitudinal direction of the second end portion 26 is directed towards the winding assembly 14, thereby reducing frictional and binding contact between the band 18 and the second end portion 26 as the band 18 is pulled therethrough. Reducing such frictional and binding contact facilitates winding of the band 18 by reducing the effort which must be exerted by the user in winding and reducing the likelihood that the band 18 will become snagged and possibly break.

The winding assembly 14 is attached to the body 12 by way of frame 36 which may comprise steel or other material of suitable strength. Frame 36 provides a distance x between the body 12 and the winding assembly 14 which is sufficient to substantially prevent mechanical interference between the band 18 and the body 12 as the band 18 is wound about the assembly 14. Preferably, the distance x is between about $\frac{1}{4}$ inch and two inches depending, for example, on the thickness of the band 18 employed. In the illustrated embodiment, the distance x is about $\frac{1}{2}$ inch which has been found to provide sufficient clearance for a broad range of materials, including standard surgical tubings.

In one embodiment of the present invention, the winding assembly 14 comprises a spool 38 which is rotatably mounted on the frame 36 and a winding engagement site 41 operatively connected to the spool 38 is provided which can be rotated by a pneumatic or electrical power motor 43, such motor being integral to or alternatively separate from the frame 36. The power tool 45 or motor 43 utilized must be capable of engaging the winding engagement site 41 in a manner so that the winding means 14 is turned or rotated, thus facilitating the accumulation of ligature material on the winding assembly 14. In one embodiment, the winding engagement site 41 comprises a suitably designed protuberance, such as a nut having several sides, or an indentation, similarly having a plurality of sides, engagable by a suitably complementary power tool 45 device that is capable of activating the winding means 14 to achieve rotation thereof. The compatible multi-sided protuberance or multi-sided indentation is configured so that engagement of the power tool 45 or motor device 43 with such protuberance or indentation will facilitate the powered rotation of the winding means 14.

In another embodiment, the powered winding of ligature material is achieved by the incorporation of a pneumatic or electrical device into the tool's 10 overall design so that a separate power tool 45 need not be interconnected or engaged with a separate powered tool. As such, the incorporation of a pneumatic or electrical powered motor 43 that is integral with the castration tool 10 is within the scope of the present invention. An illustrative embodiment of such embodiment is shown in FIGS. 8 and 9.

With reference to FIGS. 8 and 9, a pneumatic device 21 is incorporated into the handle 22 of the tool 10. An air supply 23 can be interconnected with one end of the handle 22 to operate an air piston 25 residing within the handle 22. An air control valve 27 located on the handle 22 can be used to control the winding operation so as to achieve desired winding of ligature material about the spool 38. In one embodiment, a drive linkage 29 between the pneumatic device 21 and the winding assembly 14 is provided to permit operation of a ratcheted lever 31 having an axis of rotation coincident with the axis of rotation of the spool 38. The lever 31 is attached to a ratchet mechanism 52 so that the spool 38 can be selectively rotated in alternative directions. The drive linkage 29 is operatively attached to a piston rod 33 which is driven by the air piston 25 located in the tool's handle 22. Upon operation of the air piston 25, the piston rod 33 is moved back and forth within the body 12 of the device. Through such movement the drive linkage 29 communicates with the ratcheted lever 31 to rotate the spool 38 in a desired direction. Winding of the ligature material 20 around the spool 38 can thus be accomplished by regulating the number of times the air piston 25 is forced forward and backwards, thereby ratcheting the ligature material 20 around the spool 38 to achieve a desired tension of the ligature loop 20.

In some applications, it is important to regulate the tightness or tension of a ligature loop 20 to prevent breakage thereof or to prevent injury to the animal. The tightness of ligature material can be regulated by adjusting the amount of force communicated by the rotation of the winding means 14 by a motor 43. This can be accomplished by, for example, a clutch mechanism 47 either incorporated into the winding means 14 or, alternatively, can be a feature of the power tool 45. For instance, a pneumatic power tool 45 capable of rotating the winding means 14 can be adjusted so that no further rotations occur after a predetermined tension or torque is achieved, at which point air is bled from the pneumatic power tool 45 rather than being used to rotate the winding assembly 14. The ligature material is therefore wound about the winding means 14 to a pre-determined tension, such tension regulated by a clutch mechanism 47 operatively associated with the motor 43 or in alternative embodiments, a feature of the power tool 45.

As can be readily appreciated, the rate at which the loop 20 is tightened will depend upon the diameter of the spool 38 and the speed of rotation of the spool 38. In addition, the tension which can be imparted to the band 18 by winding the band a predetermined number of times around the spool 38 or, alternatively, by gauging the tension or torque exerted on the winding assembly 14 so that at a predetermined desired tension, the spool 38 is no longer rotated. The diameter of the spool 38 can therefore be selected to allow the desired rate and degree of tightening. Although it is believed that a broad range of spool 38 diameters would provide adequate results, the illustrated spool 38 has a diameter between about ½ inch and ¾ inch. Such a diameter allows for rapid tightening of the loop 20 and allows the loop 20 to be sufficiently tightened to substantially cut off blood flow and systemic support to the body part to be removed.

The spool 38 further includes fasteners 44 to attach the band 18 to the spool 38. The fasteners 44 may comprise a slotted portion of the spool 38, a clip biased against the spool 38 or any other device by which the band 18 can be secured to the spool 38. Where an elastomeric band is employed, is it expedient to provide a fixed element closely adjacent to a surface of the spool 38 so that the band 18 can be frictionally secured therebetween. In the illustrated embodiment, the fasteners 44 comprise cantilevered rods extending inwardly from flanged end portions 46 of the spool 38. The fasteners 44 can be positioned such that the space between the spool 38 and a fastener 44 is progressively restricted from a free end 48 to a base 50 of the fastener 44. Such a configuration allows the band 18 to be quickly and reversibly secured to the spool 38 by inserting the band 18 between the spool 38 and the free end 48 and then sliding the band 18 towards the base 50 until the band 18 is securely wedged therein.

The winding engagement site 41 is interconnected to the spool 38 such that the spool 38 can be rotated by turning of the winding means 14. A ratchet assembly 52 can be employed to facilitate rapid tightening of the loop 20. The assembly 52 comprises a first ratchet and pawl mechanism 54 which cooperates with a second ratchet and pawl mechanism 56 at the opposite end of the spool 38 to allow rotation of the spool 38 in only one direction. The user can thus tighten the loop 20 through repeated turnings of the spool 38 and the pneumatic or electric winding device 43 can be adjusted so that at a desired tension, no further winding of the spool 38 occurs. The present invention therefore provides a method and device that facilitates the speedy ligation of animal parts, and thus considerably shortens the time period required to perform the ligation procedure. This spares the user from exposing himself/herself to extended periods of danger encountered when working with large animals and lessens the discomfort of the animals.

Although particular dimensions for the illustrated embodiment have been provided, it is within the scope of the present invention to have a tool body of any dimensions, thus allowing for variation of the distance between the operator and animal.

Although not shown, it will be appreciated that the ratchet assembly 52 could be eliminated and the winding engagement site 41 could instead be rigidly interconnected to the spool 38 with appropriate modification of the apparatus 10. It will be further appreciated that a winding engagement site 41 can be positioned on either or both sides of the body 12 to facilitate right hand or left hand users.

After the loop 20 has been tightened, the loop size can be maintained by securely interconnecting portions of the band 18 adjacent the loop 20. The portions may be interconnected by using an adhesive; stapling, pinning or heat sealing the band 18; binding portions of the band with wire, rope or the like; or any other suitable method for securing the loop 20. In the illustrated embodiment, a crimping assembly 16 is provided to crimp a grommet 32 after the loop 20 has been tightened, thereby securing the loop 20. The grommet 32 preferably comprises a cylindrical structure having an interior passageway sufficient to allow passage of the band 18 therethrough and can be formed from aluminum or other deformable material. During the ligation procedure, the grommet 32 is housed within a receptacle 30 of the second end portion 26. As shown most clearly in FIG. 4, the receptacle 30 can include an internal annular shoulder 60 such that the grommet 32 can be positioned by sliding the grommet 32 into the receptacle 30 until an end of the grommet 32 abuts the shoulder 60.

The grommet 32 used with the present invention can be of any desired shape and dimension to fit appropriately in the receptacle 30. The grommet 32 must be capable of being properly crimped in a manner sufficient to hold two bands 82 together so as to form a loop 20 of ligature material. The grommet 32 must retain the loop 20 in a tensive condition during the atrophy process which may take several weeks. Further, the grommet 32 is designed so as to securely fasten the ligature material without significantly damaging the material. The grommet 32 can be a completely enclosing angular structure or may alternatively be configured with side portions bendable to secure each individual end of the ligature material, thus independently fastening each end without being dependent upon the adjacency of the other end to achieve a secure loop 20. The grommet 32 may further include indexing means comprising indentations or protuberances so that the grommet 32 is properly oriented within the tool 10 to achieve a desired crimping configuration.

Figure 5:
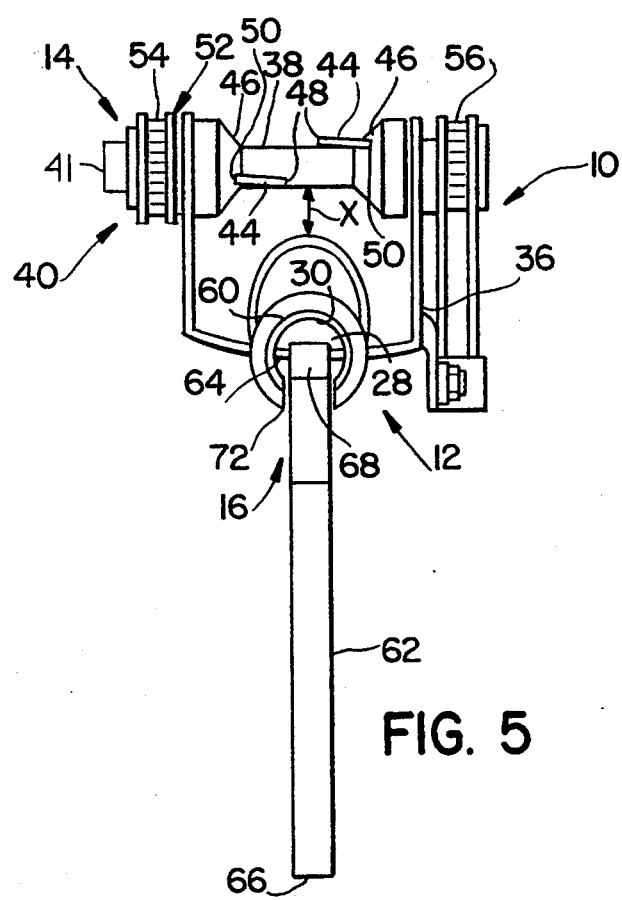
FIG. 5 is a front elevational view of the apparatus of FIG. 1 with the crimping arm in a deflected position.

The crimping assembly 16 comprises a lever 62 which is pivotally mounted on the body 12 by way of a fulcrum 64 such as a pin. The user can move the lever 62 from a retracted position (FIG. 3) to an extended position (FIGS. 4 and 5) by urging the rearward end 66 of the lever 62 downwardly as viewed in the figures. In the extended position, the forward end 68 of the lever 62 extends into the receptacle 30 to deform the grommet 32. As shown, the fulcrum 64 is preferably positioned towards the forward end 68 of the lever 62 so that a relatively small downward force exerted on the rearward end 66 of the lever 62 by the user results in a greater crimping force on the grommet 32.

The fulcrum 64 penetrates a bulge portion 70 of the lever 62 which extends through a slot 72 in the body 12. Forwardly from the fulcrum 64, the lever 62 tapers so that the lever 62 can be fully withdrawn from the receptacle 30 in the retracted position. In addition, the illustrated lever 62 includes a downwardly extending portion 74 adjacent the rearward end 66 of the lever 62 to avoid mechanical interference with a flange 76 of the handle 22 and to provide sufficient clearance between the body 12 and the lever 62 for gripping by the user. If desired, the lever 62 may be contoured for optimal handling by the user or a grip (not shown) may be interconnected with the lever 62 for this purpose.

Referring to FIGS. 6 and 7, side and front views, respectively, of an apparatus 78 constructed in accordance with the present invention are shown. The apparatus 78 includes a cutting assembly 80 for cutting the band 82 rearwardly of the grommet 84 after the loop 20 has been tightened. Any device for cutting the band 82 may be employed in accordance with the present invention. For example, a hand-held razor, scissors or other cutting tool 10 may be employed. In the illustrated embodiment, the assembly 80 comprises a razor 88 slidably mounted within a housing 90 which is interconnected to or integral with the apparatus body or frame. Preferably, the cutting assembly 80 severs the band 82 a suitable distance rearwardly of the grommet 84 to reduce the likelihood that the band 82 will be pulled through the grommet 84 after severing. In this regard, it will be appreciated that elastomeric bands tend to constrict under tension and expand after severing such that such bands may slide a distance through the grommet 84 before becoming secured therein.

The razor is slidable from a retracted position, wherein the cutting surface of the razor 88 is protectively housed within housing 90, to an extended position (as shown in phantom in FIG. 7) wherein the cutting surface of the razor 88 extends into the band passageway to cut the band 82. The razor 88 can be moved from the retracted position to the extended position by pressing downwardly on an upper surface 92 of the razor 88, such that the upper surface 92 is urged downwardly through finger cut-out 94. Preferably, the razor 88 is biased upwardly, e.g. by a spring, so that the razor 88 remains in the retracted position until the razor 88 is pressed downwardly.

In operation, a tool 10 may be employed in accordance with the present invention to ligate a body part as follows. Initially, a band of ligature material is either looped around the body part and inserted through an end portion of the tool 10 and a grommet 32 housed therein, or a loop 20 is preformed and then positioned around the body part to be ligated. End portions of the band can then be attached to a spool by sliding the end portions between fasteners and the spool such that the end portions are frictionally engaged therebetween. Although not shown in the illustrated embodiments above, it will be appreciated that it would be sufficient to attach only one end portion of the band to the spool. For example, one end portion of the band could be connected to the spool and a second end portion could be connected to the body. In this regard, attaching the band to the spool at two end portions has the advantage that the band can be tightened quickly and evenly. However, attaching the band to the spool at only one end portion and allowing the other end portion to remain stationary as the band is tightened has the advantage that the stationary end portion need not be severed from a supply of band material prior to winding the band.

After the band is secured to the spool, the band can be tightened by turning or rotating the winding means 14. The band can be tightened by operation of a pneumatic or electrical winding tool 10 that engages the winding assembly 14 to thereby cause the spool to rotate, tightening the ligature loop 20. The present invention therefore provides a method and device for tightening a loop 20 around a body part without expenditure of physical strength, such as a user's hand strength. The tightness of the loop 20 is therefore not limited by the user's hand strength, allowing for the expedited ligation of body parts.

When the loop 20 is tightened sufficiently, the loop 20 can be secured by moving a crimping lever to an extended position thereby deforming the grommet 32 so that the band portions therein are frictionally secured. Thereafter, the band may be severed with a cutting tool 10, e.g., a razor, rearwardly of the grommet 32 leaving the loop 20 attached to the body part.

The present invention has a number of advantages over other ligation methods and tools 10. First, the present invention allows a band to be tightened quickly and easily, thereby reducing the time that the animal must be restrained. In addition, the present invention allows the band to be set tightly such that blood flow and systemic support to the body part can be reliably cut off, thereby reducing the likelihood of swelling, infection, prolonged stress to the animal and/or failure of the ligation procedure. Further, because the band is progressively wound about the spool as the loop 20 is tightened, tension forces are spread relatively evenly over the band during the ligation procedure, thereby reducing the likelihood that the band will fail. It is a further advantage of the present invention that larger and stronger elastomeric materials, or relatively inelastic materials, may be used. The present invention also has ease-of-use advantages as band tightening and crimping can be accomplished with relatively little effort. Other advantages will be apparent to those skilled in the art.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for severing a body part, comprising the steps of:
    forming a loop about said body part with a band of elastomeric ligature material; and
    winding said band to tighten said loop, wherein said loop is tightened sufficiently to substantially cut off blood flow to said body part, said step of winding accomplished by using a motor to turn a winding means in a manner so that ligature material can accumulate on said winding means.

2. The method of claim 1, further comprising the step of:
passing said band elastomeric material through a grommet.

3. The method of claim 2, further comprising the step of deforming said grommet to secure said loop, after said loop is tightened.

4. The method of claim 3, wherein said step of deforming comprises pivoting a lever, wherein a portion of said lever is urged against said grommet to deform said grommet.

5. The method of claim 2, further comprising the step of cutting said band rearwardly of said grommet.

6. The method of claim 2, wherein said winding is regulated to achieve a desired tension of said elastomeric ligature material.

7. A castration tool, comprising:
means for receiving elastomeric ligature material having first and second portions;
means for winding elastomeric ligature material, said winding means operatively attached to said receiving means and being activated by a motor that turns the winding means in a manner so that elastomeric ligature material can accumulate on said winding means; and
means for securing a first portion of elastomeric ligature material to a second portion of elastomeric ligature material, said securing means operatively attached to said winding means.

8. The tool of claim 7, wherein said means for receiving comprises an elongated tool body including a longitudinal portion and first and second ends, a handle interconnected to said tool body adjacent said first end of said body, and a portion interconnected to said body adjacent said second end of said body which is angled relative to said longitudinal portion, said angled portion having an opening therein for receiving elastomeric ligature material.

9. The tool of claim 7 wherein said means for receiving comprises a receptacle for holding a grommet having a passageway sufficient to allow passage of elastomeric ligature material therethrough.

10. The tool of claim 7, wherein said means for winding comprises a spool having an axis of rotation generally transverse to a longitudinal axis of said tool.

11. The tool of claim 10 wherein said winding means further comprises a ratchet mechanism to provide for one way winding of said spool.

12. The tool of claim 7, wherein said winding means includes a spool having an axis of rotation coincident with the axis of rotation of said motor.

13. The tool of claim 7, further comprising:
means for attaching a portion of elastomeric ligature material to said winding means.

14. The tool of claim 7, further comprising:
means for attaching a first portion of elastomeric ligature material to said winding means and means for attaching a second portion of elastomeric ligature material to said receiving means.

15. The tool of claim 7, further comprising:
means for attaching firsthand second end portions of elastomeric ligature material to said winding means.

16. The tool of claim 7, wherein said means for winding comprises a spool and means for fastening elastomeric ligature material to said spool.

17. The tool of claim 16, wherein said fastening means comprises a fastener mounted to rotate in unison with the spool, wherein a space is provided between the fastener and the spool, the space being dimensioned so as to securely hold elastomeric ligature material therein.

18. The tool of claim 7, wherein said securing means comprises means for deforming a grommet so as to securely hold said first and second portions therein.

19. The tool of claim 7, wherein said securing means comprises a lever pivotally mounted on said means for receiving, wherein a grommet is deformed by pivoting said lever thereby securing elastomeric ligature material therein.

20. The tool of claim 7, wherein said means for receiving comprises an opening for receiving a band of elastomeric material.

21. The tool of claim 7, further comprising cutting means for cutting elastomeric ligature material after a loop of ligature material is tightened, said cutting means operatively attached to said tool.

22. The tool of claim 21, wherein said cutting means comprises a razor slidably mounted on said tool.

23. The tool of claim 7, wherein said motor has a mechanism capable of regulating how tight said elastomeric ligature material is wound.

24. The tool of claim 7, wherein said motor is an integral part of said tool.

25. The tool of claim 7, further comprising a clutch means for regulating how tight ligature material is wound.

26. The tool of claim 25, wherein said clutch means is adjustable.

27. The tool of claim 7, wherein said motor is separate from said tool.

28. The tool of claim 7, wherein said tool is pneumatically or electrically driven.

29. The tool of claim 7, wherein said tool is used to remove an animal body part.

30. A castration tool for tightening a loop formed from a band of elastomeric ligature material, comprising:
an elongated tool body having a handle at a rearward portion thereof and a receptacle at a forward portion thereof, the receptacle capable of holding a grommet through which elastomeric ligature material is received, wherein ligature material forms a loop forwardly of said receptacle around an animal body part;
a spool rotatably mounted on said tool body, said spool having an axis of rotation, and a winding engagement site for connection to a motor, wherein elastomeric ligature material is tightened by securing elastomeric ligature material to said spool and then rotating said spool by a motor that turns said spool in a manner so that elastomeric ligature material can accumulate thereon;
a ratchet assembly operatively associated with said spool so as to substantially prevent rotation of said spool in one direction; and
a lever pivotally mounted on said tool body for crimping a grommet, after elastomeric ligature material is tightened, thereby securing elastomeric ligature material.

31. The tool of claim 30, further comprising a clutch mechanism operatively associated with said tool.

32. The tool of claim 30, wherein said clutch mechanism is capable of regulating how tight said ligature material is wound.

* * * * *

UNITED STATES PATENT AND TRADEMARK OFFICE
CERTIFICATE OF CORRECTION

PATENT NO. : 5,403,325
DATED : April 4, 1995
INVENTOR(S) : Callicrate

It is certified that error appears in the above-identified patent and that said Letters Patent is hereby corrected as shown below:

Column 2,
Line 21, "bony" should read -- body --

Column 9,
Line 61, "firsthand" should read -- first and second --.

Signed and Sealed this

Eleventh Day of February, 2003

JAMES E. ROGAN
*Director of the United States Patent and Trademark Office*